United States Patent
Han et al.

(10) Patent No.: US 9,034,398 B2
(45) Date of Patent: May 19, 2015

(54) TRADITIONAL CHINESE DRUG COMPRISING DANSHEN EXTRACTS AND SANQI EXTRACTS AND USE THEREOF

(75) Inventors: Jingyan Han, Beijing (CN); Jun Guo, Beijing (CN); Jiying Yang, Beijing (CN); Yu Zhang, Beijing (CN); Mingxia Wang, Beijing (CN); Yuying Liu, Beijing (CN)

(73) Assignee: TASLY Pharmaceutical Group Co., LTD., Tianjin (CN)

( * ) Notice: Subject to any disclaimer, the term of this patent is extended or adjusted under 35 U.S.C. 154(b) by 0 days.

(21) Appl. No.: 13/516,209

(22) PCT Filed: Dec. 17, 2010

(86) PCT No.: PCT/CN2010/079928
§ 371 (c)(1),
(2), (4) Date: Jun. 15, 2012

(87) PCT Pub. No.: WO2011/072619
PCT Pub. Date: Jun. 23, 2011

(65) Prior Publication Data
US 2012/0251634 A1 Oct. 4, 2012

(30) Foreign Application Priority Data
Dec. 17, 2009 (CN) .......................... 2009 1 0244837

(51) Int. Cl.
| A61K 36/25 | (2006.01) |
|---|---|
| A61K 36/00 | (2006.01) |
| A61K 36/537 | (2006.01) |
| A61K 36/258 | (2006.01) |
| A61K 9/46 | (2006.01) |
| A61K 9/00 | (2006.01) |
| A61K 9/16 | (2006.01) |
| A61K 9/19 | (2006.01) |
| A61K 9/20 | (2006.01) |
| A61K 9/48 | (2006.01) |

(52) U.S. Cl.
CPC ............ *A61K 36/258* (2013.01); *A61K 9/0007* (2013.01); *A61K 9/0019* (2013.01); *A61K 9/0056* (2013.01); *A61K 9/1623* (2013.01); *A61K 9/1652* (2013.01); *A61K 9/19* (2013.01); *A61K 9/2027* (2013.01); *A61K 9/2031* (2013.01); *A61K 9/2054* (2013.01); *A61K 9/2059* (2013.01); *A61K 9/4858* (2013.01)

(58) Field of Classification Search
None
See application file for complete search history.

(56) References Cited

U.S. PATENT DOCUMENTS

| 2003/0152651 A1 | 8/2003 | Yan et al. |
| 2005/0037094 A1 | 2/2005 | Yan et al. |
| 2012/0295858 A1 | 11/2012 | Han et al. |

FOREIGN PATENT DOCUMENTS

| CN | 1470255 A | * | 1/2004 |
| CN | 1732964 | | 2/2006 |
| CN | 1732964 A | * | 2/2006 |
| CN | 101006984 A | * | 8/2007 |
| CN | 101244123 | | 8/2008 |
| EP | 1741439 | | 1/2007 |
| EP | 1741439 A1 | * | 1/2007 |
| WO | WO 2009135433 A1 | * | 11/2009 |
| WO | 2011/054301 A1 | | 5/2011 |
| WO | WO 2011/072619 | | 6/2011 |

OTHER PUBLICATIONS

Zeng et al, Influence of compatibility ratio of Fufang Danshen on the dissolution of Danshen compositions. Chinese journal of chromatography / Zhongguo hua xue hui, (Mar. 2004) vol. 22, No. 2, pp. 141-143.*
Poljanac et al, Enzymatic preparation of Danshensu. Slovenski Kemijski Dnevi, Maribor, Slovenia, Sep. 25-26, 2003, 239-245.*
International Search Report corresponding to co-pending International Patent Application Serial No. PCT/CN201007079928; dated Mar. 31, 2011 4 pages.
Zheng Qin, Peng G Chang-chun, Shen Mei-lan, Yang Ming (Key Laboratory of Modern Preparation of TCM (Ministry of Education), Jiangxi Univeristy of Traditional Chinese Medicine, Nanchang 330006, China) "Study on Compatibility of Radix ET Rhizoma Salviae Miltiorrhizae and Radix ET Rhizoma Notoginseng" vol. 15 No. 2, Dated Feb. 2009, pp. 83-86.
Bok et al., "Inhibition of arterial myogenic responses by a mixed aqueous extract of *Salvia miltiorrhiza* and *Panax notoginseng* (Pasel) showing antihypertensive effects" Korean Journal of Physiology & Pharmacology 13(4):287-293 (2009).
Kurose et al., "Inhibition of nitric oxide production. Mechanisms of vascular albumin leakage" Circulation Research 73(1):164-171 (1993).

(Continued)

*Primary Examiner* — Qiuwen Mi
(74) *Attorney, Agent, or Firm* — Nixon Peabody LLP (57) ABSTRACT

The present invention discloses a traditional Chinese drug consisting of Danshen extract and Sanqi extract, the pharmaceutical composition comprising the above traditional Chinese drug as an active component and the use thereof. The traditional Chinese drug consists of Danshen extract and Sanqi extract in a weight ratio of (2~6):(0.5~2). The invention further discloses the effect of the above traditional Chinese drug and the pharmaceutical composition comprising the above traditional Chinese drug as an active component for treating cardiac microcirculation disorder and myocardial damage induced by ischemia/reperfusion.

14 Claims, 7 Drawing Sheets

(56) References Cited

OTHER PUBLICATIONS

Lu et al., "Development of an HPLC-UV-ELSD method for quantification of multiple components of a Chinese medicine made from radix *Salvia miltiorrhiza* and *Panax notoginseng*" Chromatographia; An International Journal for Rapid Communication in Chromatography, Electrophoresis and Associated Techniques, Vieweg Verlag, WI 65(1-2):19-24 (2006).

Miao, "Transient ischemic attacks (TIAs) treated with electroacupuncture and Chinese herbal medicine" Medical Acupuncture 20(4):281-285 (2008).

Sun, "Effects of natural products on ischemic heart diseases and cardiovascular system" Acta Pharmacologica Sinica 23(12):1142 (2002).

Yan et al., "Interaction of salvianolic acids and notoginsengnosides in inhibition of ADP-induced platelet aggregation" The American Journal of Chinese Medicine 36(2):313-328 (2008).

Zhao et al., "Antioxidant activities of *Salvia miltiorrhiza* and *Panax notoginseng*" Food Chemistry, Elsevier Ltd. KL 99(4):767-774 (2006).

Yan, J., Journal of the Japan Society of Acupuncture and Moxibustion, 54(4):591-603 (2004). "Effect of Herbal Medicines and Acupuncture on Microcirculatory Disturbance.".

Huiqing Ma, "The protective effects of the calcium channel blockers on myocardial ischemia reperfusion", Medical Journal of National Defending forces in Southwest China, 1992, vol. 2 (2), p. 113-116.

* cited by examiner

*Compared to Sham, P < 0.05   #Compared to I/R group, P < 0.05

TRADITIONAL CHINESE DRUG COMPRISING DANSHEN EXTRACTS AND SANQI EXTRACTS AND USE THEREOF

CROSS-REFERENCE TO RELATED APPLICATIONS

This application is a U.S. national stage of International Patent Application No. PCT/CN2010/079928, filed Dec. 17, 2010, which claims the benefit of Chinese Patent Application No. 200910244837.X filed Dec. 17, 2009, the contents of which are each incorporated herein by reference in its entirety.

FIELD OF THE INVENTION

The present invention relates to the medical field, in particular to a traditional Chinese drug composition and the use thereof in ameliorating cardiac microcirculation disorder and myocardial damage.

BACKGROUND OF THE INVENTION

With the improvement of people's living standard and the changing of their lifestyle, cardiovascular diseases have become one main disease, which is not only threatening human health and life, but also influencing medical and financial revenue. There are about 16.5 million persons died from cardiovascular diseases per year on the worldwide. In China, the number of deaths has reached 3 million per year, accounting for 45% of the total death toll.

The clinical applications of the therapeutic methods, such as percutaneous transluminal coronary angioplasty (PTCA), cardiac surgery extracorporeal circulation, coronary artery bypass grafting, rescue and treatment of complex congenital heart diseases, valve replacement and great vessel surgery etc., have saved the lives of cardiovascular patients to a certain degree. However, the occurrence of postoperative ischemia/reperfusion (I/R) damage has become a main challenge for long-term effect of cardiovascular surgery. Besides, I/R damage caused by resuscitation after cardiac arrest, cardiovascular spasm relief and thrombolysis has also influenced on the effect of the rescue and treatment. As a result, the prevention and amelioration of myocardial I/R damage are believed to be an important aspect for improving the effect of rescue and treatment and reducing mortality of the cardiovascular diseases.

In the early stage of the myocardial I/R, the excessively released peroxides and pro-inflammatory factors from the coronary vessel endothelial cells and leukocytes, and overexpressed adhesion molecules and the like results in an adhesion between leukocytes and vascular endothelial cells. Further, those peroxides and proteases, which are released from the leukocytes adhered to vascular endothelial cells, damages the vascular endothelial cells and basement membrane, resulting in a leakage of plasma proteins. All of the edema around blood vessels induced by a leakage of plasma proteins, leukocytes emigrated from vessels, capillary occlusion caused by vascular endothelia swelling or micro-thrombus and the like can lead to the necrosis or apoptosis of peripheral myocardial cells, eventually forming myocardial infarction. Amelioration of the I/R-caused microcirculation disorder is an important aspect for reducing myocardial damage after I/R. As a result, it is extremely urgent to research and develop a medicine for preventing and improving the myocardial I/R damage.

Danshensu, namely, (3,4-dihydroxyphenyl)lactic acid, is a main water-soluble component in Radix *Salviae Militiorrhizae* (Danshen), a traditional Chinese drug. It has been confirmed in our prior researches that Danshensu had a potential for inhibiting the following: the production of peroxides in rat's mesenteric venule walls caused by I/R, the expression of leucocytes adhesion molecules CD11b/CD18, the adhesion between leucocytes and venule walls, and the leakage of plasma albumin. However, it is still unclear whether Danshensu has an influence on cardiac microcirculation disorder and myocardial damage caused by I/R. Notoginsenoside R1 is one of the main saponins of *Panax notoginseng* (Sanqi). In our previous researches, it has been verified that notoginsenoside R1 can reduce leukocytes adhered to rat's liver caused by I/R and can ameliorate microcirculation disorder of the liver. As yet, it is not known whether notoginsenoside R1 can act on cardiac microcirculation disorder and myocardial damage caused by I/R.

DESCRIPTION OF THE INVENTION

In order to solve the aforesaid technical problems, the present invention provides a traditional Chinese drug composition which can be used for preventing and ameliorating cardiac microcirculation disorder and myocardial damage caused by I/R.

The present invention further provides a use of the aforesaid traditional Chinese drug composition in a preparation of a medicine for ameliorating cardiac microcirculation disorder and myocardial damage caused by I/R.

The technical solutions of the present invention are achieved by the following aspects:

According to the present invention, said traditional Chinese drug composition consists of Radix *Salviae Militiorrhizae* (Danshen) extract and *Panax Notoginseng* (Sanqi) extract in a weight ratio of (2~6):(0.5~2).

Preferably, said traditional Chinese drug composition consists of Danshen extract and Sanqi extract in a weight ratio of (1~4):1.

Preferably, said traditional Chinese drug composition consists of Danshen extract and Sanqi extract in a weight ratio of 4:1. The traditional Chinese drug composition according to the present invention can remarkably ameliorate a red blood cell (RBC) velocity in the venules of the heart coronary vessels and heart perfusion flow in the rats caused by I/R, and can reduce the percentage of the myocardial infarction area after I/R.

The Danshen extract according to the present invention is preferably a water-soluble extract having strong pharmacological effects. The effective components in the water-soluble extract include Danshensu and polyphenolic acids. Wherein, said Danshen extract is preferably Danshensu, i.e., (3,4-dihydroxyphenyl)lactic acid, which is a hydrolysate of caffeic acid. Danshensu (5 mg/kg body weight (BW)/h) can transiently ameliorate the red blood cell (RBC) velocity in the venules of the heart coronary vessels and heart perfusion flow in the rats caused by I/R, and can reduce the percentage of the myocardial infarction area after I/R.

Said Danshensu is commercially available, or can be extracted by conventional methods. For example, Danshen is extracted by an ultrasonic extraction, followed by extracting with water and precipitating with ethanol, and then the resultant extract was purified by removing impurities with polyamide and/or macroporous resin adsorption column. The preparation methods for Danshen extract disclosed in Chinese Patent Application Nos. CN02144600, CN02133727 and CN90107488 can also be selected.

The Sanqi extract according to the present invention is yellow powder, which can be dissolved in methanol and water, but insoluble in ethyl ether, etc. It has significant effects on blood lipid regulation and immune regulation. As shown in the experiments, Sanqi extract has good assistant therapy action for the patients suffered from immunologic maladjustment and dyslipidemia without any toxic and side effects. Said Sanqi extract according to the present invention is one or more selected from the group consisting of Notoginsenoside R1, Ginsenoside Rb1, Ginsenoside Re and Ginsenoside Rg1. Preferably, said Sanqi extract is Notoginsenoside R1.

The above-said Sanqi extract can be obtained by purchasing as a raw material in the market, or by a conventional method or self-developed process, for example, the methods disclosed in Chinese Patent Application Nos. CN1412163A and CN200510044534.5 can be used.

According to the present invention, said compositions are expressed in the weight ratios, the weight ratio of the components can be increased or decreased in the corresponding proportion during the production, for example, the weight unit of the components can be in kilogram or ton during a large-scale production and in milligram (mg) during a small-scale production. The weight of components may be correspondingly increased or decreased, but the weight ratio between different components remains unchanged.

The present invention also provides a pharmaceutical composition prepared by using said traditional Chinese drug composition as an active component, and the pharmaceutical composition can be other medicines or health products. Wherein, the other medicines or health products comprises 0.1~99.9 wt % of the active component, and the balanced is pharmaceutically acceptable carrier(s).

According to the present invention, combined with various types of carriers, such as excipients or adjuvants, said herbal composition can be made into certain dosage forms. Usually, the dosage form is suitable to be administrated orally, intramuscularly, intraperitoneally, subcutaneously or intravenously. Further, the suitable dosage form to be orally-administrated can be tablets (such as orally disintegrating tablets), capsules (such as soft capsules), drop pills, granules, oral solutions, powders, pastes, pellets, pills; suppositories and the rapid or sustained release preparations thereof, dry powder inhalations, aerosols and gels. The dosage form suitable to be intramuscularly or intravenously-administrated can be injections or lyophilized powders for injection, and the like. Preferably, said dosage form is the dosage form suitable to be orally-administrated, such as capsules, tablets, oral solutions, granules, pills, powders, pellets or pastes, etc.

According to the present invention, said excipients include binding agents, bulking agents, diluents, tablet-pressing agents, lubricants, disintegrating agents, colorants, flavoring agents, wetting agents, and if necessary, coating agents so that the tablets can be coated.

Suitable bulking agents include cellulose, mannitol, lactose and other analogous bulking agents. Suitable disintegrating agents include starch, polyvinylpyrrolidone (PVP) and starch derivatives (such as sodium starch glycollate). Suitable lubricants include, such as magnesium stearate. Suitable pharmaceutically acceptable wetting agents include sodium dodecyl sulfate.

Usually, oral solid preparations can be prepared by conventional methods, such as blending, filling and tablet-pressing, etc. Being blended repeatedly allows the active substance distribute uniformly into those compositions having a large amount of bulking agent.

According to the present invention, oral liquid preparations can be, for example water-soluble or oil-soluble suspensions, solutions, emulsions, syrups or elixirs, or dried products that can be reconstituted with water or other suitable carriers before using. The liquid preparations can contain conventional additive(s), for example, suspending agents, e.g. sorbitol, syrup, methylcellulose, gelatin, hydroxyethyl cellulose, carboxymethyl cellulose, aluminum stearate gel or hydrogenated edible fat; emulsifying-agents, e.g. lecithin, sorbitan monoleate or arabic gum; non-aqueous carriers which can include edible oil, e.g. almond oil, fractionated coconut oil, butyraceous esters such as esters of glycerol, propylene glycol or ethanol; and preservatives, e.g. methyl paraben, nipasol or sorbic acid. And if necessary, conventional scenting agents or colorants can be included.

As for the drop pills, appropriate pharmaceutically acceptable carriers can be selected and added. Said carriers are selected from sugar alcohol, e.g. mannitol, sorbitol, xylitol; amino acid, e.g. cysteine hydrochloride, methionine, glycine; Vitamin C; EDTA disodium salt, EDTA calcium sodium salt; inorganic salts, e.g. carbonates, acetates, phosphates of the monovalent alkali metals or the aqueous solutions thereof, sodium chloride, potassium chloride, sodium pyrosulfite, sodium bisulfite, sodium thiosulfate, calcium carbonate, calcium bicarbonate; stearates, e.g. calcium stearate, magnesium stearate; inorganic acids, e.g. hydrochloric acid, sulfuric acid, phosphoric acid; organic acids, e.g. acetic acid; organic acid salts, e.g. sodium lactate; oligosaccharides, polysaccharides, celluloses and derivatives thereof, e.g. maltose, glucose, fructose, dextran, sucrose, lactose, cyclodextrin (such as β-cyclodextrin), starch; mercaptoacetic acid; silicon derivatives; alginate; gelatin; PVP, glycerol; Tween-80; agar; surfactants; polyethylene glycol; phospholipids materials; Kaolin; talc powder etc.

As for the injections, the prepared liquid unit dosage form contains the traditional Chinese drug composition of the present invention as an active component and sterile carrier(s). According to the type of the carrier and concentration of the active component, said active component can be dissolved or suspended. Generally, the solutions are prepared by dissolving the active component in the carrier(s), sterilizing by filtering, loading into a suitable vial or ampoule, and sealing. Some pharmaceutically acceptable vehicles, e.g. local anesthetics, preservatives and buffering agents can also be added into the carriers. In order to improve the stability of the injections, the composition of the present invention can be frozen after being loaded into the vial and then treated in vacuum to remove water.

According to the present invention, the use of the traditional Chinese drug composition, and preparations or health products thereof, in a preparation of a medicine for ameliorating cardiac microcirculation disorder and myocardial damage caused by I/R was shown in the following experimental examples.

EXPERIMENTAL EXAMPLES

1. Materials and Methods 1.1 Medicines and Reagents

Danshensu was obtained from Fengshanjian Pharmaceutical Inc. (Kunming, China) with a lot number of 09010413. Notoginsenoside R1 was obtained from Fengshanjian Pharmaceutical Inc. (Kunming, China) with a lot number 08090318. Both of the medicines were stored at 4° C. in a dark place. Before the experiment, they were dissolved with normal saline to prepare a solution in an adequate concentration of 1.25 mg/ml for intravenous drip.

FITC-Albumin (a conjugate of bovine serum albumin and fluorescein isothiocyanate), analytically pure, was obtained from Sigma (Lot number: Ag771-1G). It was prepared into a solution at 10 mg/ml with normal saline before the experiment, which was stored at 4° C. and used up within 2 weeks. Before the experiment, the solution was prepared into a solution at 2 mg/ml and stored at room temperature. The lot number of TTC (2,3,5-triphenyl tetrazolium chloride) was 2836B041, which was prepared with phosphate buffer into a solution at 0.375%(g/ml), stored at room temperature and used up within 1 month.

1.2 Animals

SD male rats weighing 250±10 g were purchased from Animal Center of Peking University Health Science Center (animal certification number was SCXK (Jing) 2006-0001). The rats were fed ad-libitum fed normal diet and water under the conditions of 24±1° C. and a relative humidity of 55±5%. The care of all animals complied with the Guide for the Care of Laboratory Animals issued by the Ministry of the Health.

1.3 Establishment of the I/R Model

The rats were anesthetized by intramuscularly injecting 20 wt % urethane (1.25 g/kg) and fixed in the supine position. Neck skin was incised and anterior cervical muscles were separated to expose the trachea. Tracheal intubation was performed. Another end of the intubation was attached to a Small Animal Ventilator (ALC-V8, Shanghai Aoteshai Biology Science and Technology Limited Company, Shanghai, China) so as to carry out pressure breathing under the following conditions: a respiratory ratio of 1:1, a respiratory frequency of 75 times/min and a tidal volume of 12 mL/kg. The rectal temperature, measured with YSI REF 401 (Yellow Spring, Ohio, USA), was maintained at 37~37.5° C. by using a thermal blanket. The chest was sterilized and opened at the intercostal space between 2nd~4th ribs near the left and right sternal border to expose the heart. The ⅜ curved needle threaded with 3-0 suture was used to pass through the site at 1~2 mm below the juncture of the pulmonary artery cone and the left atrial appendage. The suture was ligated. A polyethylene tubule was placed between the silk suture and myocardial tissue, the silk suture was tensed to cause ischemia. Ligature was released 30 min later to establish an I/R model.

1.4 Administration

Sham operation group (Sham group): normal saline was administrated by intravenous drip (1 ml/h) 20 min before the experiment and continued until the end of the entire experiment.

I/R model group (I/R group): normal saline was administrated by intravenous drip (1 ml/h) 20 min before the experiment and continued until the end of the entire experiment.

Danshensu+I/R group (DLA+I/R group): a Danshensu aqueous solution (in normal saline, 1.25 mg/ml) was administrated at a dosage of 5 mg/kg BW/h by intravenous drip 20 min before the experiment and continued until the end of the entire experiment.

Notoginsenoside R1+I/R group (R1+I/R group): a Notoginsenoside R1 aqueous solution (in normal saline, 1.25 mg/ml) was administrated at a dosage of 5 mg/kg BW/h by intravenous drip 20 min before the experiment and continued until the end of the entire experiment.

Danshensu:R1(4:1)+I/R group (DR(4:1)+I/R group): an aqueous solution of Danshensu and Notoginsenoside R1 at a weight ratio of 4:1, dissolved in normal saline (1.25 mg/ml, namely, in the solution, the concentration of Danshensu is 1 mg/ml and the concentration of Notoginsenoside R1 is 0.25 mg/ml), was administrated at a dosage of 5 mg/kg BW/h (namely, in the total dosage, the dosage of Danshensu is 4 mg/kg BW/h and the dosage of Notoginsenoside R1 is 1 mg/kg BW/h) by intravenous drip 20 min before the experiment and continued until the end of the entire experiment.

Danshensu:R1 (1:1)+I/R group (DR(1:1)+IR group): an aqueous solution of Danshensu and Notoginsenoside R1 at a weight ratio of 1:1, dissolved in normal saline (1.25 mg/ml, namely, in the solution, the concentration of Danshensu is 0.625 mg/ml and the concentration of Notoginsenoside R1 is 0.625 mg/ml), was administrated at a dosage of 5 mg/kg BW/h (namely, in the total dosage, the dosage of Danshensu is 2.5 mg/kg BW/h and the dosage of Notoginsenoside R1 is 2.5 mg/kg BW/h) by intravenous drip 20 min before the experiment and continued until the end of the entire experiment.

Danshensu:R1 (0.25:1)+I/R group (DR(0.25:1)+IR group): an aqueous solution of Danshensu and Notoginsenoside R1 at a weight ratio of 0.25:1, dissolved in normal saline (1.25 mg/ml, namely, in the solution, the concentration of Danshensu is 0.25 mg/ml and the concentration of Notoginsenoside R1 is 1.0 mg/ml), was administrated at a dosage of 5 mg/kg BW/h (namely, in the total dosage, the dosage of Danshensu is 1 mg/kg BW/h and the dosage of Notoginsenoside R1 is 4 mg/kg BW/h) by intravenous drip 20 min before the experiment and continued until the end of the entire experiment.

1.5 Diameters of the Venules of Heart Coronary Vessels and Red Blood Cell (RBC) Velocities Therein A high speed camera (ultimate APX PHOTRON, FAST-CAM, US) connected with a upright microscope (BX51WI, Olympus, Japan) was used with ×10 objective lens to select and observe the venules with a diameter of 30~50 μm through a monitor (20PF5120, PHLIPS, US) under a vertical light. Heart coronary vessel microcirculation had been recorded by a CD video recorder (DVR-560H, PHLIPS, US). The high speed camera was set at a rate of 500 frames·s$^{-1}$. The diameter of the venules and RBC velocity under a same visual field were recorded before ischemia, 30 min after ischemia, 30 min after reperfusion and 60 min after reperfusion. Recordings were replayed at 25 frames·s$^{-1}$, diameters of the arterioles and the venules as well as RBC velocities were measured with Image-Pro Plus 5.0 software. RBC velocities in the rat's heart arterioles and venules were expressed as "mm/s", and the diameters of the rat's heart arterioles and venules were expressed as "μm".

1.6 Measurement of Plasma Albumin Leakage from the Venules of Heart Coronary Vessels At 60 min after I/R, FITC-labeled plasma albumin at a dose of 50 mg/kg BW/h was slowly administrated via femoral vein bolus injection. Under an upright fluorescence microscope (USS-301, Leica, US), fluorescence image of each group was recorded with SIT camera by using a light at 455 nm as an exciting light and a mercury lamp (100 W) as an emission source. FITC fluorescence intensities inside the venules and the adjacent extravascular interstitial substance were measured with Image-Pro Plus 5.0 software, respectively. The results were expressed as a ratio of the FITC fluorescence intensity inside the venules to that of the adjacent extravascular interstitial substance in the same visual field.

1.7 Measurement of Blood Flow Volume of Heart

Blood flow volumes on the surface of heart before ischemia, 5 min, 30 min after ischemia, and 5 min, 30 min, 60 min after reperfusion had been recorded by a computer-aided laser Doppler perfusion imager (LDPI) (PeriScan PIM3, PERIMED, Sweden). Images were measured and the data were evaluated with LDPIwin software. Change rate of blood flow volume of the heart was calculated by taking the blood flow volume before I/R as a baseline.

1.8 Calculation of Myocardial Infarction Area 60 min after reperfusion, the heart of the rat was taken out (n=6, each group), and cut from the cardiac apex along the direction parallel to the atrioventricular septum into 5 pieces of slices in thickness of 1 mm. The obtained slices were placed into TTC (0.375 g/ml) which was dissolved in PBS, and incubated at 37° C. for 15 min in order to be stained by TTC. Non-infarction region was stained as red and the infarction region as white. Myocardial pictures were photographed by using a digital sight (DS-5M-U1, NIKON, Japan), and myocardial infarction area was calculated with Image-Pro plus 5.0 software (Media Cybemetrics Inc, USA). The myocardial infarction area was expressed as a percentage of the myocardial infarction region area to the total cardiac area.

1.9 Statistical Analysis

SPSS11.5 software package was used for a statistics analysis. Data of each group were expressed as $\bar{x}\pm SE$, and calculated by using One-Way ANOVA. $P<0.05$ represents that the difference had statistical significance.

2 Results

Figure 1:
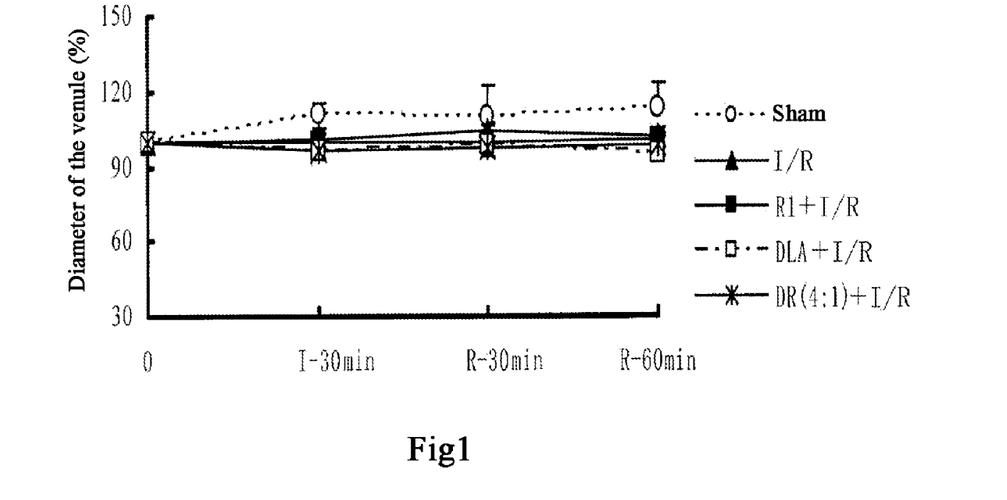
FIG. 1 illustrates the change in the diameter of the venules of the heart coronary vessels in the rats of Sham group, I/R group, R1+I/R group, DLA+I/R group and DR+I/R group.

2.1 Effect on Diameters of the Venules of Heart Coronary Vessels after Myocardial Ischemis/Reperfusion FIG. 1 shows a continuous change in the diameters of the venules of the heart coronary vessels in the rats of Sham group, I/R group, R1+I/R group, DLA+I/R group and DR(4:1)+I/R group. No significant change in the diameters of the venules of the heart coronary vessels in the rats of Sham group had been detected during the entire observation. Similarly, during the entire observation, there was also no significant change in the diameters of the venules of the heart coronary vessels in the rats of I/R group, R1+I/R group, DLA+I/R group and DR(4:1)+I/R group.

Figure 2:
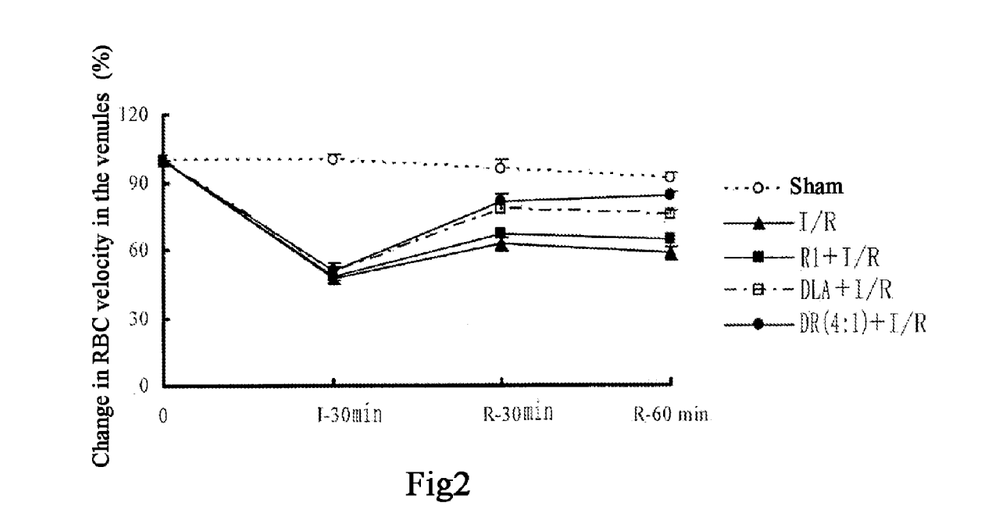
FIG. 2 illustrates the change in RBC velocity in the venules of the heart coronary vessels in the rats of Sham group, I/R group, R1+I/R group, DLA+I/R group and DR(4:1)+I/R group.

2.2 Effect on RBC Velocity of the Venules and Arterioles in Rat's Heart after Myocardial I/R FIG. 2 shows a continuous change in RBC velocity in the venules of the heart coronary vessels in the rats of Sham group, I/R group, R1+I/R group, DLA+I/R group and DR(4:1)+I/R group. No significant change in the RBC velocity in the venules of the heart coronary vessels in the rats of Sham group has been detected during the entire observation. RBC velocity in the venules of the heart coronary vessels in the rats of I/R group decreases significantly at the beginning of reperfusion, which is continued to decrease until the end of observation. From 30 min after I/R, Danshensu shows a significantly inhibitory effect on the decreased RBC velocity caused by I/R. However, this inhibitory effect does not further improved until 60 min after reperfusion. Notoginsenoside R1 does not display a significantly inhibitory effect on the decreased RBC velocity in the venules of the heart coronary vessels in the rats caused by I/R. From 30 min after reperfusion, the DR has a significant inhibitory effect on the decreased RBC velocity caused by I/R, and the inhibitory effect has continued to enhance until 60 min after reperfusion.

Figure 3A:
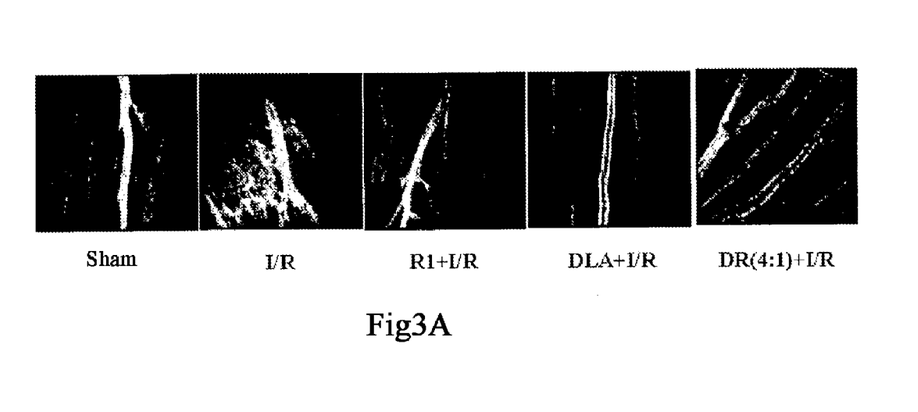
FIG. 3A represents the images of FITC-labeled plasma albumin leakage in the rats of each group at 60 min after reperfusion.

2.3 Effect on Plasma Albumin Leakage of the Rat's Heart after Myocardial I/R FIG. 3A shows the status of albumin leakage from the venules of the heart coronary vessels at 60 min after reperfusion in the rats of Sham group, I/R group, R1+I/R group, DLA+I/R group and DR (4:1)+I/R group. A small amount of FITC-labeled albumin leakage from the venules of the coronary vessels has been observed in the rats of Sham group. A significant FITC-labeled albumin leakage from the venules of the coronary vessels can be observed in the rats of I/R group. A FITC-labeled albumin leakage from the venules of the coronary vessels can also be observed in the rats of R1+I/R group and DLA+I/R group. By contrast, the FITC-labeled albumin leakage from the venules of the coronary vessels is remarkably suppressed in the rats of the DR group.

Figure 3B:
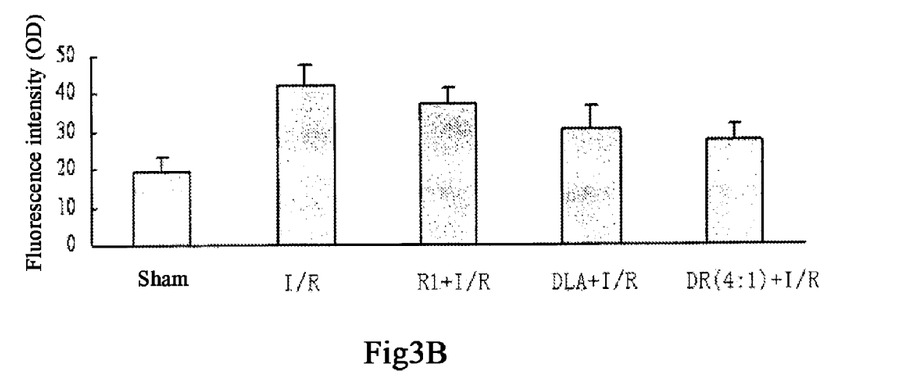
FIG. 3B represents a ratio between the fluorescence intensity of FITC-labeled albumin outside the venules of the heart coronary and that inside of the venules of the heart coronary vessels at 60 min after reperfusion in each group.

FIG. 3B shows a ratio between the fluorescence intensity of FITC-labeled albumin outside the venules of the heart coronary and that inside of the venules of the heart coronary vessels 60 min after reperfusion in the rats of Sham group, I/R group, R1+I/R group, DLA+I/R group and DR (4:1)+I/R group. Compared to the ratio in the rats of Sham group, the ratio in I/R group remarkably increases. Significant inhibitory effect on FITC-labeled albumin leakage has not been observed by R1 and DLA. However, the DR significantly inhibits FITC-labeled albumin leakage from the venules of the heart coronary vessels in rats.

2.4 Effect on Heart Blood Flow Volume after Myocardial I/R

Figure 4A:
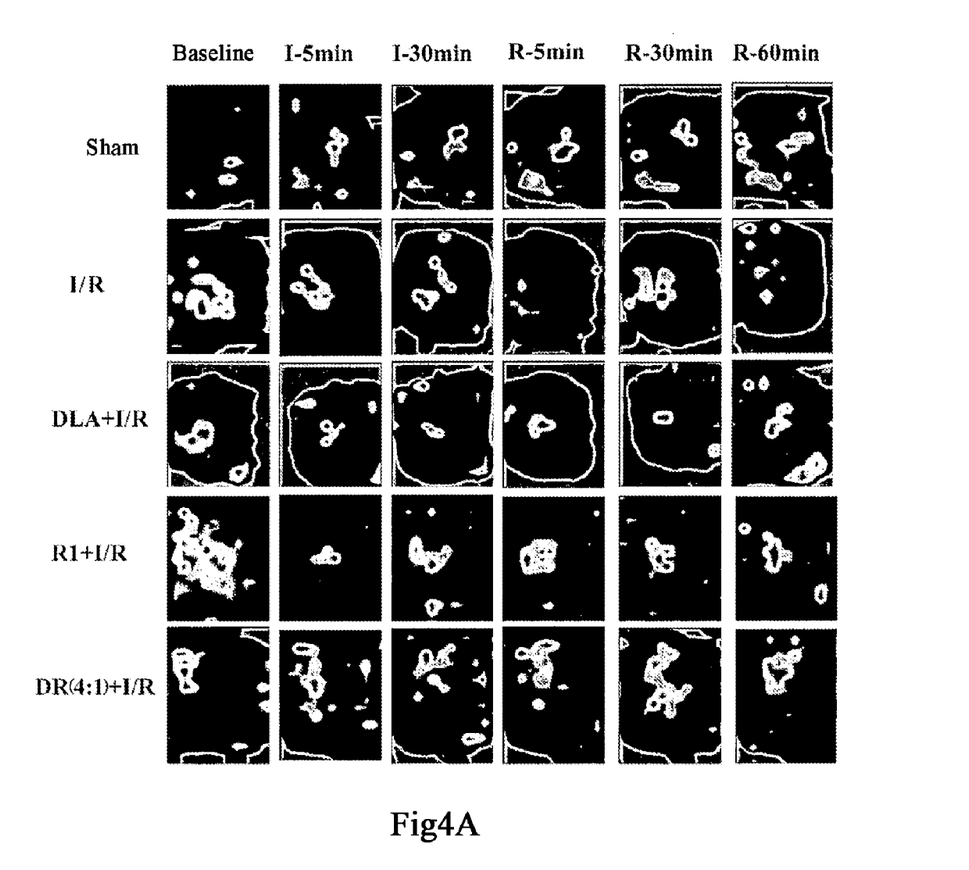
FIG. 4A illustrates the images of the heart blood flow volume measured by LDPI in the rats of Sham group, I/R group, DLA+I/R group, R1+I/R group, and DR(4:1)+I/R group.

FIG. 4A shows the images of heart blood flow volume of the rats in Sham group, I/R group, DLA+I/R group, R1+I/R group and DR (4:1)+I/R group measured by Laser Doppler Perfusion Imaging. There is no significant change in heart blood flow volume in the rats of Sham group during the entire observation. In I/R group, the blood flow volume decreased obviously from the beginning to 60 min after reperfusion. In R1+I/R group and DLA+I/R group, compared to I/R group, the blood flow volume is regained to some extent at 30 min and 60 min after reperfusion. In DR (4:1)+I/R group, the blood flow volume has been regained obviously from 5 min after reperfusion.

Figure 4B:
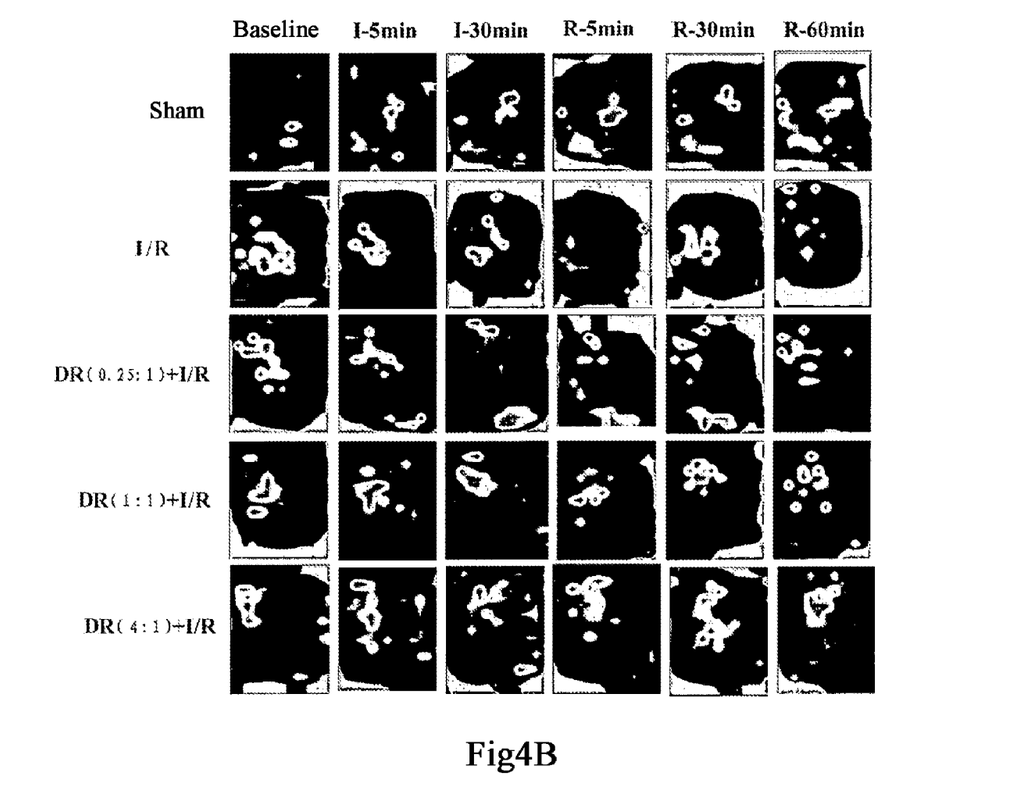
FIG. 4B illustrates the images of the heart blood flow volume measured by LDPI in the rats of Sham group, I/R group, DR(0.25:1)+I/R group, DR(1:1)+I/R group and DR(4:1)+I/R group.

FIG. 4B shows the images of heart blood flow volume of the rats in Sham group, I/R group, DR(0.25:1)+I/R group, DR(1:1)+I/R group and DR(4:1)+I/R group measured by Laser Doppler Perfusion Imaging. There is no significant change in the heart blood flow volume in the rats of Sham group during the entire observation. In I/R group, the blood flow volume is decreased obviously from the beginning to 60 min after reperfusion. Danshensu is combined with R1 in different ratios of 0.25:1, 1:1 and 4:1, which are tested at a total dosage of 5 mg/kg Bw/h. It shows that the heart blood flow volume can be regained by any combination of Danshensu and R1. Further, with the gradual increase in the proportion of Danshensu (namely, the ratio increased from 0.25:1 to 1:1, even to 4:1), such regaining effect shows a gradually growing tendency. Wherein, it is believed that the regaining effect is most significant when the ratio of Danshensu to R1 is 4:1.

Figure 5A:
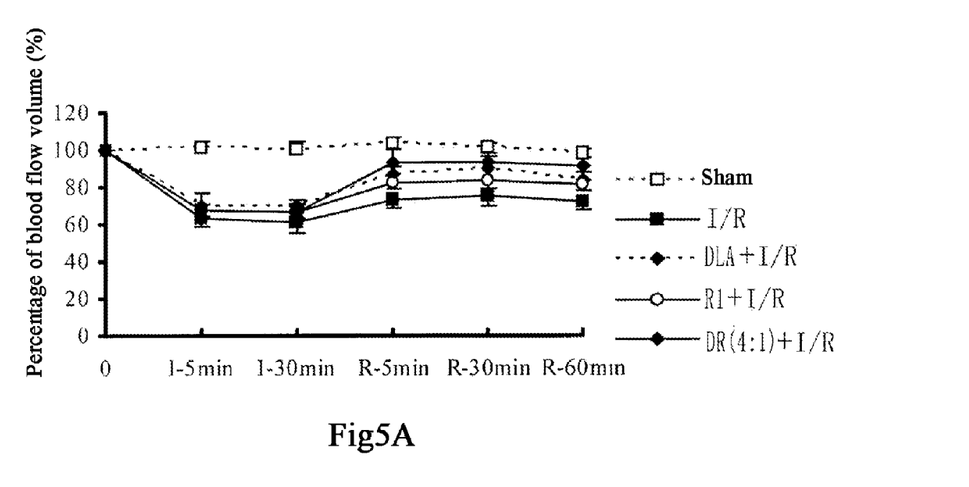
FIG. 5A illustrates the images of the continuous change in the heart blood flow volume in the rats of Sham group, I/R group, DLA+I/R group, R1+I/R group, and DR(4:1)+I/R group.

FIG. 5A shows a continuous change in the heart blood flow volume in the rats of Sham group, I/R group, DLA+I/R group, R1+I/R group and DR(4:1)+I/R group. No significant change in the heart blood flow volume in the rats of Sham group has been observed during the entire observation. In I/R group, the blood flow volume is reduced to 63% of the baseline during ischemia, which is regained to 73% of the baseline after the beginning of reperfusion, and regained to 72% of the baseline at 60 min after reperfusion. R1 has not been observed to have significantly inhibitory effect on the decrease of the heart blood flow volume in the rats after I/R. Danshensu (DLA) has a significantly inhibitory effect on the decrease of the heart blood flow volume in the rats after I/R at 5 min after reperfusion. However, the DR starts to significantly inhibit the decrease of heart blood flow volume in the rats after I/R from 5 min after reperfusion.

Figure 5B:
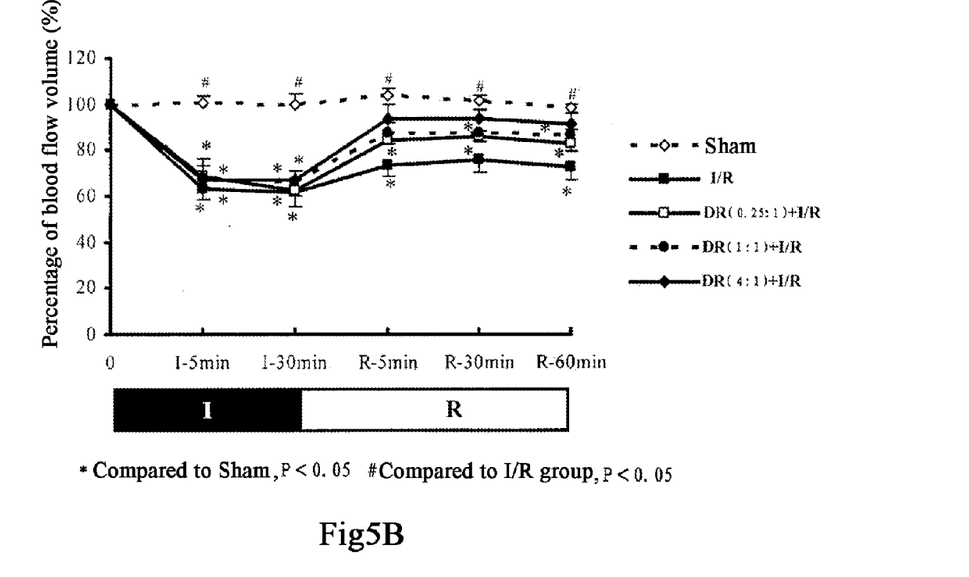
FIG. 5B illustrates the images of the continuous change in the heart blood flow volume in the rats of Sham group, I/R group, DR(0.25:1)+I/R group, DR(1:1)+I/R group and DR(4:1)+I/R group.

FIG. 5B shows a continuous change in the heart blood flow volume in the rats of Sham group, I/R group, DR(0.25:1)+I/R group, DR(1:1)+I/R group and DR(4:1)+I/R group. No significant change in the heart blood flow volume in the rats of Sham group has been observed during the entire observation. In I/R group, the heart blood flow volume is reduced to 63% of the baseline during ischemia, which is regained to 73% of the baseline after the beginning of reperfusion, and regained to 72% of the baseline at 60 min after reperfusion. Danshensu is combined with R1 in different ratios of 0.25:1, 1:1 and 4:1, which are tested at a total dosage of 5 mg/kg Bw/h. It is shown that with the gradual increase in the proportion of Danshensu (namely, the ratio is increased from 0.25:1 to 1:1, even to 4:1), the inhibitory effect on the decrease of the heart blood flow volume in the rats after I/R gradually increases. Wherein, it is believed that the inhibitory effect is most significant when the ratio of Danshensu to R1 is 4:1.

2.5 Effect on Myocardial Infarction Area in Rat Caused by Myocardial I/R

Figure 6A:
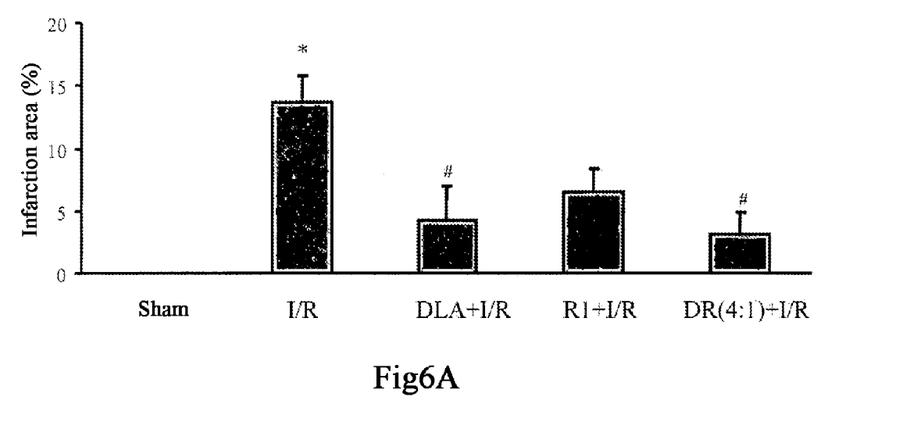
FIG. 6A illustrates the comparison between the percentages of the myocardial infarction area at 60 min after reperfusion in the rats of Sham group, I/R group, DLA+I/R group, R1+I/R group and DR(4:1)+I/R group.

FIG. 6A shows the percentages of the myocardial infarction area to the total cardiac area at 60 min after reperfusion in the rats of Sham group, I/R group, DLA+I/R group, R1+I/R group and DR(4:1)+I/R group. No infarction region has been observed in the rats of Sham group. A larger white-stained infarction region is clearly observed from the slices of the heart in the rats of I/R group. In contrast, the infarction region in R1 group is observed to be decreased slightly, and the infarction regions in DLA+I/R group and DR (4:1)+I/R group decreased obviously. It can be clearly seen that, compared to Sham group, the percentage of the myocardial infarction area in the rats of I/R group increases significantly. R1 has not significantly inhibited the increase of the myocardial infarction area percentage in the rats after I/R. However, DLA and DR(4:1) can significantly suppress the increase of the myocardial infarction area percentage caused by I/R.

Figure 6B:
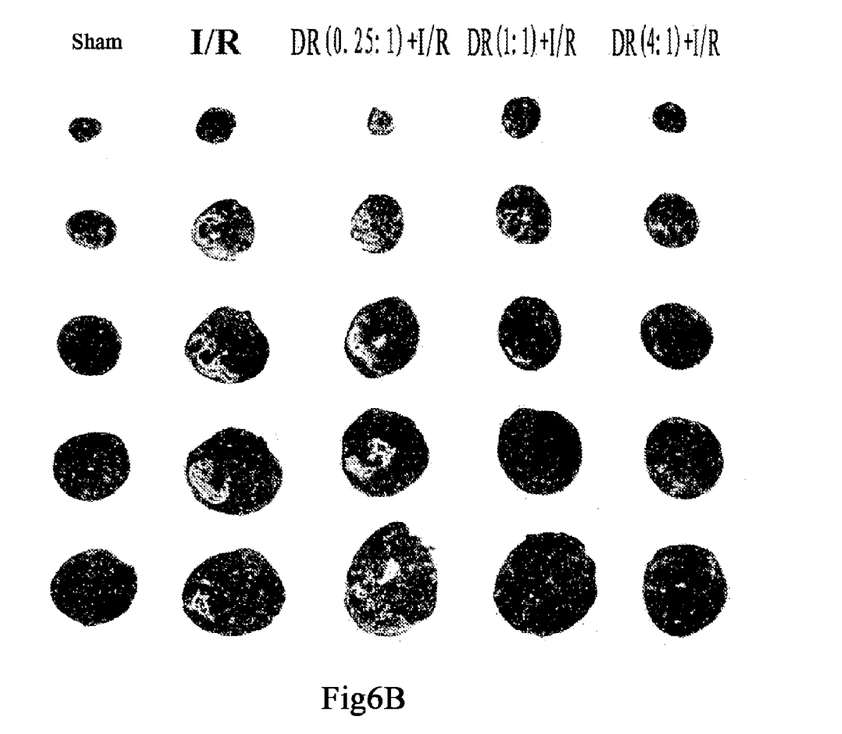
FIG. 6B illustrates the images of the myocardial slices at 60 min after reperfusion in the rats of Sham group, I/R group, DR(0.25:1)+I/R group, DR(1:1)+I/R group and DR(4:1)+I/R group.

FIG. 6B shows the images of the myocardial slices at 60 min after reperfusion in the rats of Sham group, I/R group, DR(0.25:1)+I/R group, DR(1:1)+I/R group and DR(4:1)+I/R group. From the top to the bottom, it is represented in the images that 5 pieces of slices in a thickness of 1 mm had been obtained by cutting the heart along the direction parallel to the atrioventricular septum from the cardiac apex. The obtained slices were placed into TTC which was dissolved in PBS (0.375 g/ml), and incubated at 37° C. for 15 min in order to be stained by TTC. Non-infarction region was stained as red and the infarction region as white. Myocardial pictures were photographed using a digital sight (DS-5M-U1, NIKON, Japan). Compared to Sham group, there is a significant increase in the percentage of myocardial infarction area in the rats of I/R group. Danshensu was combined with R1 in different ratios of 0.25:1, 1:1 and 4:1, which were tested at a total dosage of 5 mg/kg Bw/h. It is shown that the combination of Danshensu and R1 can reduce myocardial infarction area. Moreover, with the gradual increase in the proportion of Danshensu (namely, the ratio increases from 0.25:1 to 1:1, even to 4:1), myocardial infarction area is shrinked gradually. It is hardly to observe the myocardial infarction in the ratio of 4:1.

Figure 6C:
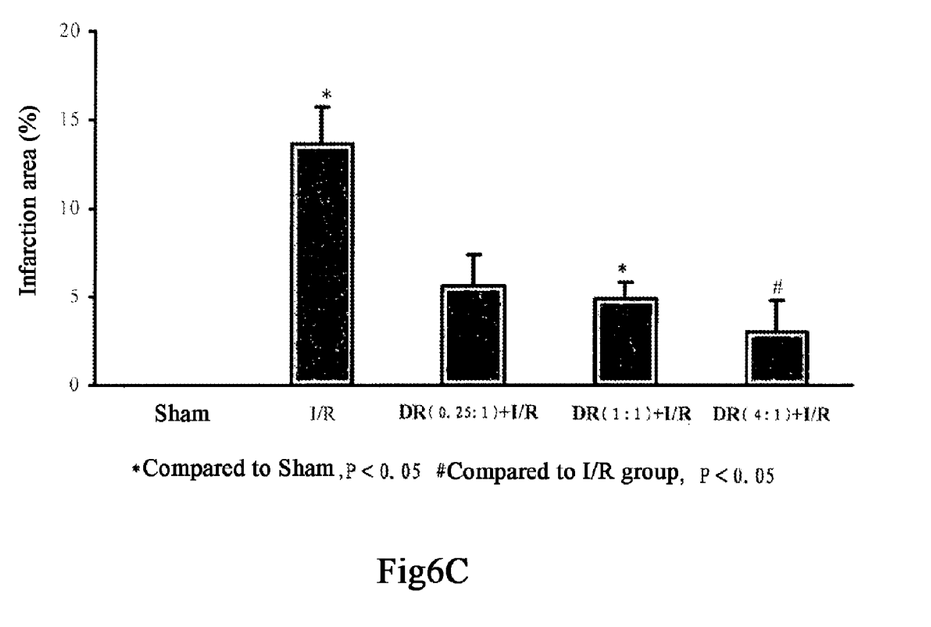
FIG. 6C illustrates the percentages of the myocardial infarction area to the total cardiac area at 60 min after reperfusion in the rats of Sham group, I/R group, DR(0.25:1)+I/R group, DR(1:1)+I/R group and DR(4:1)+I/R group.

FIG. 6C shows the percentages of the myocardial infarction area to the total cardiac area at 60 min after reperfusion in the rats of Sham group, I/R group, DR(0.25:1)+I/R group, DR(1:1)+I/R group and DR(4:1)+I/R group. Compared to Sham group, there is a significant increase in myocardial infarction area percentage in I/R group. Danshensu is combined with R1 in different ratios of 0.25:1, 1:1 and 4:1, which are tested at a total dosage of 5 mg/kg BW/h. It is shown that the combination of Danshensu and R1 can inhibit the increase of the myocardial infarction area percentage caused by I/R. Compared to Sham group, there is a significant difference ($P<0.05$) in inhibiting the increase of myocardial infarction percentage caused by I/R in DR(1:1)+I/R group. Additionally, compared to I/R group, there is a significant difference ($P<0.05$) in inhibiting the increase of myocardial infarction percentage caused by I/R in DR(4:1)+I/R group. Especially, it should be noted that the inhibitory effect is most remarkable when the ratio of Danshensu to R1 is 4:1.

DESCRIPTION OF DRAWINGS

FIG. 3 illustrates the results of FITC-labeled albumin leakage from the venules of the heart coronary vessels at 60 min after reperfusion in the rats of Sham group, I/R group, R1+I/R group, DLA+I/R group and DR(4:1)+I/R group. Wherein.

EXAMPLES

The following examples are given only for purpose of illustration and do not intend to limit the scope of the invention in any way.

Example 1

8 g of Danshensu and 2 g of Notoginsenoside R1 were provided and well mixed to prepare the traditional Chinese drug composition of the present invention.

Example 2

2.5 g of Danshensu and 2.5 g of Notoginsenoside R1 were provided and well mixed to prepare the traditional Chinese drug composition of the present invention.

Example 3

2 g of Danshensu and 0.5 g of Ginsenoside Re were provided and well mixed to prepare the traditional Chinese drug composition of the present invention.

Example 4

120 g of Danshen extract and 10 g of Sanqi extract were provided and well mixed to prepare the traditional Chinese drug composition of the present invention.

Example 5

8 g of Danshensu, 2 g of Notoginsenoside R1 as well as starch, sodium carboxymethyl cellulose and talc powder were provided and well mixed, granulated and pressed to prepare tablets, according to the conventional tablet preparation methods.

Example 6

10 g of Danshensu, 10 g of Notoginsenoside R1 and 10 g of starch were provided, into which 100 g of PEG was added, well mixed, melted, and loaded into a drop pill machine to prepare drop pills.

Example 7

2 g of Danshen extract and 0.5 g of Notoginsenoside R1 were provided, into which 5 wt % crospovidone, 0.1 wt % magnesium stearate, and 50 wt % microcrystalline cellulose (said weight percentage was the percentage of the weight of each individual vehicle to the total weight of all of the raw materials) were added, a soft material was prepared by using an ethanol solution, granulated and air-dried at 60° C. to give granules. The granules were sifted and pressed into tablets, thereby orally disintegrating tablets were obtained.

Example 8

20 g of Danshen extract and 20 g of Sanqi extract was provided, into which starch, sucrose and magnesium stearate in a total amount of 40 g were added to produce granules. The granules were loaded into capsule shells to give capsules.

Example 9

2 g of Danshensu, 0.5 g of Notoginsenoside R1, 4.5 g of glucose, 0.9 g of sodium thiosulfate and 1 ml of distilled water were well mixed, lyophilized and separately loaded into 500 vials to give powders for injection.

Example 10

3 g of Danshen extract and 0.5 g of Notoginsenoside R1 were provided, into which 5 wt % crospovidone, 0.1 wt % magnesium stearate, and 50 wt % microcrystalline cellulose (said weight percentage was the percentage of the weight of each individual vehicle to the total weight of all of the raw materials) were added, a soft material was prepared with an ethanol solution, granulated and air-dried at 60° C. to give granules. The granules were sifted and pressed into tablets, thereby orally disintegrating tablets were obtained.

Example 11

60 g of Danshensu, 10 g of Notoginsenoside R1, and 10 ml of benzyl alcohol were provided, into which water for injection was added to a total volume of 100 ml, and thus injections were prepared.

Example 12

50 g of Danshen extract, 10 g of Ginsenoside Rb1, 3.0 g of starch, 12.5 g of microcrystalline cellulose, 2.0 g of colloidal silicon dioxide, 1.56 g of talc powder and 1.0 g of magnesium stearate were provided, these components were mixed in the aforesaid ratio, sifted through No. 5 sieve, well mixed and pressed into tablets, and 1000 tablets were obtained.

Example 13

120 g of Danshensu and 20 g of Notoginsenoside R1 were mixed well to give a traditional Chinese drug composition. 1 weight part of said traditional Chinese drug composition, 6.4 parts of sucrose powder and 1.6 parts of dextrin were provided, granulated, and the granulates were pressed into blocks and dried to produce granules.

Example 14

1 weight part of the composition of Example 1, 3 weight parts of sucrose, 1.25 weight parts of dextrin and a proper amount of ethanol were used to give granules, the obtained granules were dried and sifted, and then loaded into capsule shells to form capsules.

Example 15

30 g of Danshen extract, 10 g of *Panax notoginseng* saponins and edible vegetable oil were mixed. After well stirred, the oil solution was prepared for later use.
100 g of gelatin, 30 g of glycerol and 130 g of water were provided. A proper amount of water was added into the gelatin to form a gelatin solution. The obtained gelatin solution was placed into a tank, into which the above-obtained oil solution was poured. The mixture of the gelatin solution and the oil solution was dripped by using liquid paraffin as a coolant liquid to give soft capsules.

Example 16

25 g of Danshen extract and 25 g of Notoginsenoside R1 were mixed well to obtain the traditional Chinese drug composition of the present invention. The obtained composition was mixed with a proper amount of sodium bicarbonate, citric acid, fumaric acid, sodium cyclamate, PEG and lactose, and the obtained mixture was prepared by the conventional tablet preparation methods to prepare effervescent tablets.

Example 17

120 g of Danshen extract and 10 g of Ginsenoside Rg1 were mixed well, into which 1300 g of calcium carbonate and 100 g of starch were added and mixed well. The mixture was sifted and loaded into capsule shells to prepare 10000 capsules.

Example 18

120 g of Danshen extract, 10 g of Notoginsenoside R1 and 500 g of PEG-4000 were provided and mixed, and drop pills were prepared according to the conventional methods. Wherein, a drip tube having an inner diameter of 3.3 mm and an outer diameter of 5.1 mm was selected, the above mixture was dripped into methyl silicone oil at a speed of 60-70 drops per min. The drop pills were collected and the coolant liquid was removed with filter paper. The weight of each pill was 50 mg.

What is claimed is:

1. A traditional Chinese drug composition consisting of Danshen extract and Sanqi extract in a weight ratio of (2~6):(0.5~2), wherein said Sanqi extract is one or more selected from the group consisting of Notoginsenoside R1, Ginsenoside Rb1, Ginsenoside Re and Ginsenoside Rg1, and wherein said Danshen extract is Danshensu.

2. A pharmaceutical composition comprising the traditional Chinese drug composition according to claim 1 as an active component, wherein said pharmaceutical composition comprises 0.1~99.9 wt % of the active component, and the balanced is pharmaceutically acceptable carrier(s).

3. The pharmaceutical composition according to claim 2, wherein said pharmaceutical composition is tablets, capsules, drop pills, granules, oral solutions, powders, pastes, pellets, pills, suppositories, dry powder inhalations, aerosols, gels, injections or lyophilized powders for injection.

4. The pharmaceutical composition according to claim 3, wherein said tablets are orally disintegrating tablets or effervescent tablets, said capsules are soft capsules.

5. The traditional Chinese drug composition according to claim 1, wherein said traditional Chinese drug composition consists of Danshen extract and Sanqi extract in a weight ratio of (1~4):1.

6. The traditional Chinese drug composition according to claim 1, wherein said traditional Chinese drug composition consists of Danshen extract and Sanqi extract in a weight ratio of 4:1.

7. The traditional Chinese drug composition according to claim 1, wherein said Sanqi extract is Notoginsenoside R1.

8. A method for ameliorating cardiac microcirculation disorder caused by ischemia/reperfusion, treating myocardial damage and/or myocardial infarction caused by ischemia/reperfusion, treating myocardial damage prior to or after an interventional treatment, inhibiting microcirculation disorder with albumin leakage, or inhibiting albumin leakage from venules in a subject in need thereof, the method comprising an act of administrating to a subject a pharmaceutically effective dosage of a traditional Chinese drug composition consisting of Danshen extract and Sanqi extract in a weight ratio of (2~6):(0.5~2), wherein the pharmaceutical composition comprises, as an active component, the traditional Chinese drug composition consisting of Danshen extract and Sanqi extract in a weight ratio of (2~6):(0.5~2), wherein said pharmaceutical composition comprises 0.1~99.9 wt % of the active component, and the balance of the pharmaceutical composition comprises one or more pharmaceutically acceptable carriers.

9. The use method according to claim 8, wherein said traditional Chinese drug composition consists of Danshen extract and Sanqi extract in a weight ratio of (1~4):1.

10. The according to claim 8, wherein said traditional Chinese drug composition consists of Danshen extract and Sanqi extract in a weight ratio of 4:1.

11. A method for ameliorating cardiac microcirculation disorder caused by ischemia/reperfusion, treating myocardial damage and/or myocardial infarction caused by ischemia/reperfusion, treating myocardial damage prior to or after an interventional treatment, inhibiting microcirculation disorder with albumin leakage, or inhibiting albumin leakage from venules in a subject in need thereof, the method comprising an act of administrating to a subject a pharmaceutically effective dosage of a traditional Chinese drug composition consisting of Danshen extract and Sanqi extract in a weight ratio of (2~6):(0.5~2), wherein the pharmaceutical composition comprises, as an active component, the traditional Chinese drug composition consisting of Danshen extract and Sanqi extract in a weight ratio of (2~6):(0.5~2), wherein said pharmaceutical composition comprises 0.1~99.9 wt % of the active component, and the balance of the pharmaceutical composition comprises one or more pharmaceutically acceptable carriers, and wherein said pharmaceutical composition comprises tablets, capsules, drop pills, granules, oral solutions, powders, pastes, pellets, pills, suppositories, dry powder inhalations, aerosols, gels, injections or lyophilized powders for injection.

12. The method according to claim 11, wherein said Sanqi extract is Notoginsenoside R1.

13. The method according to claim 11, wherein said traditional Chinese drug composition consists of Danshen extract and Sanqi extract in a weight ratio of (1~4):1.

14. The method according to claim 11, wherein said traditional Chinese drug composition consists of Danshen extract and Sanqi extract in a weight ratio of 4:1.

* * * * *

UNITED STATES PATENT AND TRADEMARK OFFICE
CERTIFICATE OF CORRECTION

PATENT NO. : 9,034,398 B2
APPLICATION NO. : 13/516209
DATED : May 19, 2015
INVENTOR(S) : Jingyan Han et al.

Page 1 of 1

It is certified that error appears in the above-identified patent and that said Letters Patent is hereby corrected as shown below:

IN THE CLAIMS

On Column 14, Line 22 (Claim 9, Line 1), delete the word "use"

On Column 14, Line 25 (Claim 10, Line 1), insert -- method -- before the word "according"

Signed and Sealed this
Sixth Day of October, 2015

Michelle K. Lee
*Director of the United States Patent and Trademark Office*